US012601660B2

(12) United States Patent
Reardon et al.

(10) Patent No.: US 12,601,660 B2
(45) Date of Patent: Apr. 14, 2026

(54) FIXATIVE SOLUTION AND METHOD OF PREPARATION OF BIOLOGICAL SAMPLE

(71) Applicant: Apacor Limited, Wokingham (GB)

(72) Inventors: Paul Reardon, Hersham (GB); Robert Reardon, London (GB); Christopher Fisher, Wokingham (GB)

( * ) Notice: Subject to any disclaimer, the term of this patent is extended or adjusted under 35 U.S.C. 154(b) by 1011 days.

(21) Appl. No.: 17/267,168

(22) PCT Filed: Aug. 14, 2019

(86) PCT No.: PCT/GB2019/052287
§ 371 (c)(1),
(2) Date: Feb. 9, 2021

(87) PCT Pub. No.: WO2020/035688
PCT Pub. Date: Feb. 20, 2020

(65) Prior Publication Data
US 2021/0341361 A1     Nov. 4, 2021

(30) Foreign Application Priority Data
Aug. 14, 2018   (GB) ..................................... 1813255

(51) Int. Cl.
*G01N 1/30* (2006.01)
*C12Q 1/04* (2006.01)

(52) U.S. Cl.
CPC ................. *G01N 1/30* (2013.01); *C12Q 1/04* (2013.01); *G01N 2001/307* (2013.01)

(58) Field of Classification Search
CPC ....... G01N 1/30; G01N 2001/307; C12Q 1/04
See application file for complete search history.

(56) References Cited

U.S. PATENT DOCUMENTS

| | | | | |
|---|---|---|---|---|
| 3,997,656 | A | 12/1976 | Wertlake et al. | |
| 4,946,669 | A * | 8/1990 | Siegfried .................. | G01N 1/30 |
| | | | | 435/40.52 |
| 5,401,625 | A | 3/1995 | Robinson | |
| 9,968,101 | B2 * | 5/2018 | Modak ................... | A01N 59/16 |
| 2002/0090380 | A1 * | 7/2002 | Singh Khanuja .... | A61K 36/534 |
| | | | | 424/725 |

FOREIGN PATENT DOCUMENTS

| | | |
|---|---|---|
| CA | 1029309 A | 4/1978 |
| CN | 106596211 A | 4/2017 |
| CN | 106855475 A | 6/2017 |
| EP | 0311035 | 4/1989 |
| EP | 3 112 864 | 1/2017 |
| KR | 20020088235 A | 11/2002 |
| RU | 2536502 | 12/2014 |
| RU | 2630983 | 9/2017 |
| SU | 1314251 A1 | 5/1987 |
| WO | WO 00/11947 | 3/2000 |
| WO | 2006106245 A1 | 10/2006 |
| WO | WO-2017083729 A2 * | 5/2017 .............. G01N 1/30 |

OTHER PUBLICATIONS

"School of Veterinary Pathology: Histological Fixative", published online Apr. 15, 2014 at URL: //diyhpl.us/~bryan/irc/protocol-online/protocol-cache/histfix.htm, submitted with IDS filed Mar. 21, 2022 (Year: 2014).*
Australian Patent Office, Examination Report, App. No. 2019322103 (Mar. 11, 2022).
School of Veterinary Pathology: "Histological Fixative" (Apr. 15, 2014). URL: https://webarchive.org/web/2014*http://diyhpl.us/~bryan/irc/protocol-online/protocol-cache/histfix.htm>.
E.T. Abdel-Malek: "Menthol Relaxation of Helminths Before Fixation," Journal of Parasitology, vol. 37, No. 3, pp. 321 (1951).
Praskash et al: "To Study the Effects of Various Fixatives on Liver—A Histological Study," Scholars Journal of Applied Medical Sciences, vol. 5, Issue 12 (2017).
International Searching Authority: International Search Report and Written Opinion, Intl. App. No. PCT/GB2019/052287 (Nov. 13, 2019).
School of Veterinary Pathology: "Histological fixative," URL: http://www.bristol.ac.uk/vetscience/services/pathology/ (Jul. 20, 2005).
UK Intellectual Property Office, Combined Search and Examination Report, GB1813255.5 (2019).
Federal Institute of Industrial Property, Search Report, with English translation, App. No. 2021106369 (Oct. 7, 2021).

* cited by examiner

*Primary Examiner* — Terry A Mckelvey
*Assistant Examiner* — Andrew T Moehlman
(74) *Attorney, Agent, or Firm* — Walters & Wasylyna LLC

(57)     ABSTRACT

A fixative contains carboxylic acid, preferably acetic acid, for parasitological samples. An exemplary aqueous fixative solution for parasitological samples comprises: a) a C2 to C6 carboxylic acid (preferably acetic acid) at a concentration of 0.5M or greater; and b) a C2 to C6 carboxylate salt or halide salt at a concentration of 0.02M or greater, preferably 0.04M or greater. An optional composition comprises 1.3M acetic acid, 12 mM sodium benzoate, 0.9% calcium chloride, 0.9% calcium bromide, 100 µg/ml menthol and 350 µg/ml thymol. The fixative is free of formaldehyde or other hazardous compounds, and exhibits good killing and staining properties when used with parasitological samples such as ova and helminths.

5 Claims, No Drawings

FIXATIVE SOLUTION AND METHOD OF PREPARATION OF BIOLOGICAL SAMPLE

This application is the U.S. national phase entry of Intl. App. No. PCT/GB2019/052287 filed on Aug. 14, 2019, which claims priority from GB1813255.5 filed on Aug. 14, 2018. The entire contents of Intl. App. No. PCT/GB2019/052287 and GB1813255.5 are incorporated herein by reference.

FIELD OF THE INVENTION

The present invention relates to a fixative solution for the histological fixation of biological samples and to a method of preparation of biological samples for examination, for example, by microscopy.

BACKGROUND

The invention is concerned particularly but not exclusively with a fixative solution suitable for fixation of living organisms, especially parasitological samples, such as helminth ova or *Giardia lamblia* for example.

A fixative solution for such applications is required to kill the organism (which may be pathogenic) and to preserve their cellular structure so that they can subsequently be examined microscopically, typically after staining with a stain such as Trypan blue, Lugol's iodine or Trichrome stain, for example. The microscopic appearance of the sample after staining is affected by the fixative solution, but it is difficult or impossible to predict the effect of a given formulation of fixative on the staining properties.

Formaldehyde has been widely used in fixative solutions (for example, in aqueous solution as formalin) but is toxic, carcinogenic and generally hazardous to the environment.

Other fixatives have been used but in many cases are also hazardous.

More recently, non-hazardous fixatives have been developed, for example, as disclosed in GB 2528426A (Reardon) and WO92/19951A (Streck Lab) but there remains a need for fixative solutions which will reliably kill parasitical organisms such as helminths which, having a tough outer layer, are highly resistant to the penetration of fixative. Cell death is difficult to achieve in a short time if highly toxic chemicals such as formaldehyde are ruled out.

An object of the present invention is therefore to provide a relatively non-hazardous fixative that is suitable for histological fixing of parasitological samples in particular.

A further object of the invention is to provide a fixative and method of preparation of biological samples that results in good staining properties.

SUMMARY

Accordingly, the invention provides an aqueous fixative solution for biological samples comprising:
- a) a C2 to C6 carboxylic acid at a concentration of 0.5M or greater
- b) a C2 to C6 carboxylate salt or halide salt at a concentration of 0.02M or greater, preferably 0.04M or greater.

Optionally, said C2 to C6 carboxylic acid is acetic acid.

Optionally, the concentration of C2 to C6 carboxylic acid is 0.9M or greater, more preferably 1.3M or greater. Optionally, the concentration of the of C2 to C6 carboxylic acid is no greater than 3.5M.

It has been found that such concentrations of carboxylic acid (particularly acetic acid) result in a rapid killing of biological organisms such as helminth ova, for example, without requiring a toxic additive such as formaldehyde.

In an optional, yet preferred embodiment, the concentration of acetic acid is below 10% w/v. A concentration below this limit is classified as non-corrosive.

The carboxylate salt or halide salt of component b) may for example be the salt of an alkali or alkaline earth metal or of ammonium other cation that confers reasonable solubility.

Optionally, component b) is a calcium or magnesium halide salt.

More preferably, component b) comprises calcium chloride at a concentration of at least 0.06M, preferably at least 0.08M, preferably at least 0.1M, and/or calcium bromide at a concentration of at least 0.06M, preferably at least 0.08M, preferably at least 0.1M.

It has been found that such halide salts help preserve the cellular structure, possibly an osmoregulatory effect involving the halide salts counteracting the turgor effect of the carboxylic acid.

Optionally, the fixative further comprises: c) a bacteriostatic or fungistatic concentration of benzoic acid or sorbic acid or a salt thereof.

Optionally, component c) is a benzoate salt at a concentration of at least 5 mM, more preferably at least 10 mM.

Component c) as defined above may help to preserve the sample against decomposition.

Optionally, the fixative further comprises: d) a biocidal essential oil component in a concentration of at least 50 μg/ml.

The biocidal essential oil may for example be bacteriostatic or bactericidal or fungistatic or fungicidal.

Optionally, said biocidal essential oil component d) is one or more of: menthol, thymol, pulegol, dihydrocarveol, piperitol, menthone, menthene, o-cymene, p-cymene, citronellal, carvacrol, eugenol, 4-carvo-menthol (termpinen-4-ol), allicin or camphor. Optionally, the essential oil component is present in its naturally-occurring stereoisomeric or enantiomeric form.

Desirably said biocidal essential oil component d) comprises menthol and thymol.

It has been found that such essential oils facilitate cell death and thus shorten the time needed for fixing.

In preferred, yet optional embodiments:
- i) said carboxylic acid component a) is acetic acid at a concentration of 0.8M to 1.75M,
- ii) said halide salt component b) is calcium chloride at a concentration of 70 to 100 mM plus calcium bromide at a concentration of 30 mM to 50 mM and
- iii) said benzoic acid salt component c) is at a concentration of 5 mM to 15 mM benzoate.

In particularly preferred, yet still optional embodiments:
- i) said carboxylic acid component a) is acetic acid at a concentration of 1.2M to 1.75M,
- ii) said halide salt component b) is calcium chloride at a concentration of 70 to 100 mM plus calcium bromide at a concentration of 30 mM to 50 mM and
- iii) said benzoic acid salt component c) is at a concentration of 5 mM to 15 mM benzoate.

The above embodiments advantageously may result in particularly good staining properties.

In a further preferred embodiment:
- i) said carboxylic acid component a) is acetic acid at a concentration of 0.8M to 1.75M, ii) said halide salt component b) is calcium chloride and/or calcium bromide at a total concentration of from 1.0 to 4.5M and iii) said benzoic acid salt component c) is at a concentration of 5 mM to 125 mM benzoate.

In certain preferred embodiments component b) is a halide salt at a concentration of 0.3M to 6M, preferably 1M to 5M, most preferably 1M to 4M.

Such embodiments have been found suitable for use as flotation solutions, having a density sufficiently great to float cysts or ova or other organisms of interest, thereby facilitating their separation and identification.

In such embodiments the fixative optionally includes a non-polar solute which increases the density of the fixative solution to above 1.1 g/ml, preferably above 1.2 g/ml. most preferably from 1.2 g/ml to 1.4 g/ml.

Preferably the non-polar solute is a soluble carbohydrate, preferably a sugar, preferably sucrose or glucose or fructose or maltose, or any combination thereof.

An additional aspect of the invention for which protection is sought provides a method of preparing a biological sample for examination comprising fixing the sample with an aqueous fixative solution as defined above.

Optionally, the biological sample is a living organism. Optionally, the biological sample is a parasitological sample.

In a preferred embodiment the biological sample is stained after fixing, for example, with an azo dye, or with iodine, or with a trichrome stain. Other stains can also be used.

Other preferred features are defined in the claims.

Within the scope of this application it is expressly intended that the various aspects, embodiments, examples and alternatives set out in the preceding paragraphs, in the claims and/or in the following description, and in particular the individual features thereof, may be taken independently or in any combination. That is, all embodiments and/or features of any embodiment or example can be combined in any suitable way and/or combination, unless such features are incompatible. The applicant reserves the right to change any originally filed claim or file any new claim accordingly, including the right to amend any originally filed claim to depend from and/or incorporate any feature of any other claim although not originally claimed in that manner.

DETAILED DESCRIPTION

A study was conducted to validate the effectiveness of a number of formulations of fixative in accordance with the invention in order to determine both their effectiveness to denature a cell (i.e. make inert from an infectious perspective) and to preserve cellular morphology for a prolonged period of time.

To achieve this, three types of stain were used, namely:

1. Lugol's Iodine staining to determine morphology
2. Trypan Blue staining to determine viability
3. Trichrome stain commonly used laboratory procedure.

Initially all substances were tested using a live sample of *Giardia lamblia*, which is a flagellated protozoan parasite commonly found around the world. Its abundance in numbers and delicate internal structures made this a suitable candidate for testing. Samples of *Trichuris suis* (whipworm) were also tested with the most viable formulation (Example 8) to see mainly whether the fixative was able to denature a typical helminth ova in an acceptable amount of time.

Example 1

200 ml of fixative was prepared with the following formulation:

185 ml distilled water
15 ml of Glacial Acetic Acid (7.5% solution—1.3M)
0.06 g Sodium Benzoate—2 mM
2.22 g Calcium Chloride—100 mM

Example 2

200 ml of fixative was prepared with the following formulation:

181 ml distilled water
19 ml of Glacial Acetic Acid (9.5% solution—1.65M)
0.36 g Sodium Benzoate—12 mM
3.00 g Calcium Chloride—100 mM
4.72 g Calcium Bromide

Example 3

200 ml of fixative was prepared with the following formulation:

181 ml distilled water
19 ml of Glacial Acetic Acid (9.5% solution—1.65M)
0.36 g Sodium Benzoate—12 mM
1.8 g Calcium Chloride—0.9%
1.8 g Calcium Bromide 0.9%

Example 4

200 ml of fixative was prepared with the following formulation:

190 ml distilled water
10 ml of Glacial Acetic Acid (5% solution—0.87M)
0.36 g Sodium Benzoate—12 mM
1.8 g Calcium Chloride—0.9%
1.8 g Calcium Bromide 0.9%

Example 5

200 ml of fixative was prepared with the following formulation:

181 ml distilled water
19 ml of Glacial Acetic Acid (9.5% solution—1.65M)
0.36 g Sodium Benzoate—12 mM
1.8 g Calcium Chloride—0.9%
1.8 g Calcium Bromide 0.9%
0.04 g Menthol crystals—200 µg/ml (around half of maximum solubility)
0.125 g Thymol—625 µg/ml (around 70% of maximum solubility)

Example 6

200 ml of fixative was prepared with the following formulation:

181 ml distilled water
19 ml of Glacial Acetic Acid (9.5% solution—1.65M)
0.36 g Sodium Benzoate—12 mM
1.8 g Calcium Chloride—0.9%
1.8 g Calcium Bromide 0.9%
0.02 g Menthol crystals—100 µg/ml (around a quarter of max solubility)
0.07 Thymol—350 µg/ml (around 39% of maximum solubility)

Example 7

200 ml of fixative was prepared with the following formulation:

190 ml distilled water
10 ml of Glacial Acetic Acid (5% solution—0.87M)
0.36 g Sodium Benzoate—12 mM
1.8 g Calcium Chloride—0.9%
1.8 g Calcium Bromide 0.9%
0.02 g Menthol crystals—100 µg/ml (around a quarter of max solubility)
0.07 Thymol—350 µg/ml (around 39% of maximum solubility)

Example 8

200 ml of fixative was prepared with the following formulation:

185 ml distilled water
15 ml of Glacial Acetic Acid (7.5% solution—1.3M)
0.36 g Sodium Benzoate—12 mM
1.8 g Calcium Chloride—0.9%
1.8 g Calcium Bromide 0.9%
0.02 g Menthol crystals—100 µg/ml (around a quarter of max solubility)
0.07 Thymol—350 µg/ml (around 39% of maximum solubility)

Example 9

200 ml of fixative was prepared with the following formulation:

185 ml distilled water
15 ml of Glacial Acetic Acid (7.5% solution—1.3M)
0.36 g Sodium Benzoate—12 mM
1.8 g Calcium Chloride—0.9%
1.8 g Calcium Bromide 0.9%
0.04 g Menthol crystals—200 µg/ml (around a quarter of max solubility)

Example 10

200 ml of fixative was prepared with the following formulation:

185 ml distilled water
15 ml of Glacial Acetic Acid (7.5% solution—1.3M)
0.36 g Sodium Benzoate—12 mM
1.8 g Calcium Chloride—0.9%
1.8 g Calcium Bromide 0.9%
0.07 Thymol—350 µg/ml (around 39% of maximum solubility)

Example 11

200 ml of fixative was prepared with the following formulation:

185 ml distilled water
15 ml of Glacial Acetic Acid (7.5% solution—1.3M)
0.36 g Sodium Benzoate—12 mM
1.8 g Calcium Chloride—0.9%
1.8 g Calcium Bromide 0.9%
0.2 ml Triton X-100—0.001%
(The use of Trition® surfactant negates the use of ELISA).

Example 12

Live *Giardia* samples were received and checked for morphology and to ensure correct cellular structure etc.

200 µl of Live *Giardia* were inculcated into each of the test solutions (3.3 ml) contained within a Mini Parasep SF® faecal parasite concentrator device.

This was carried out in duplicate, with:
a. One sample containing just the fixative (Sample 1); and
b. One sample containing the fixative mixed with a consistent sample of raw stool (Sample 2)

This was immediately followed by centrifugation at 400 g for 2 minutes. A 15 µl sample was then taken from the base of each sedimentation tube to be mounted on a microscope slide with 15 µl of Trypan blue stain added. As viability of the cysts was the main reason for this step, each sample was centrifuged immediately after the addition of the Live *Giardia*, and mounted directly after centrifugation.

Samples were left for a period of 24 hours and then 15 µl was taken to check morphology with Lugol's iodine and Trypan Blue of Sample 1.

Samples were left for a period of 48 hours and then 15 µl was once again taken to check morphology with Lugol's iodine of Sample 1.

Samples were left for a period of 5 days and then 15 µl was once again taken to check morphology with Lugol's iodine of both samples.

Trichrome stains were conducted for all samples which still showed good morphology, with samples being taken from Sample 1.

Further morphology testing was carried out for all samples which passed this point after a period of 2 months.

The results for the formulations of the above Examples are shown in the Table 1.0 below, together with comparative results for 10% formalin, the commercially available fixatives SAF (formaldehyde-based, containing methanol and also 2% acetic acid), a fixative solution containing methanol, ethanol, isopropanol, zinc sulphate and 4.8% acetic acid (sold under the trademark Alcorfix™), PVA (containing methanol, ethanol and zinc sulphate) and a fixative solution containing 1-(cis-3-chloroallyl)-3,5,7-triaza-1-azoniaadamantane chloride (sold under the trademark Safefix™), and also distilled water, as a control.

TABLE 1.0

| Fixative | Cell viability after 2 mins (Trypan blue) | Cell viability after 24 hours (Trypan blue) | Cell structure after 24 hours (Lugol's Iodine) | Cell structure after 48 hours (Lugol's Iodine) | Cell structure after 1 week (Lugol's Iodine) | Cell structure after 1 week (Trichrome stain) | Cell structure after 2 months (Lugol's Iodine) |
|---|---|---|---|---|---|---|---|
| 10% Formalin | Clear (cross-linking - test invalid) | | Good structure | Excellent structure | Good structure | Good definition | Good structure |

TABLE 1.0-continued

| Fixative | Cell viability after 2 mins (Trypan blue) | Cell viability after 24 hours (Trypan blue) | Cell structure after 24 hours (Lugol's Iodine) | Cell structure after 48 hours (Lugol's Iodine) | Cell structure after 1 week (Lugol's Iodine) | Cell structure after 1 week (Trichrome stain) | Cell structure after 2 months (Lugol's Iodine) |
|---|---|---|---|---|---|---|---|
| SAF | Clear (cross-linking - test invalid) | | Excellent structure | Excellent structure | Excellent structure | Reasonable definition | Acceptable structure |
| Alcorfix | Minimal blue in cell wall (start of cell death) | Dark blue ingress (Cell death) | Excellent structure | Excellent structure | Excellent structure | Good definition | Excellent structure |
| PVA | Clear (Cell viable) | Dark blue ingress (Cell death) | Excellent structure | Good structure | Excellent structure | Good definition | Excellent structure |
| SafeFix | Clear (Cell viable) | Clear (Cell appears viable) | Acceptable structure | Excellent structure | Good structure | | Poor structure |
| Distilled water | Clear (Cell viable) | Clear (Cell viable) | Excellent structure | Acceptable structure | Poor structure | Poor definition | Poor/Complete cellular degeneration |
| Example 1 | Dark blue in cell wall (Cell death) | Dark blue in cell wall and light blue cytoplasm (Cell death) | Excellent structure | Excellent structure | Excellent structure | Good definition | Good structure |
| Example 2 | Dark blue in cell wall (Cell death) | Dark blue in cell wall and light blue cytoplasm (Cell death) | Excellent structure | Excellent structure | Excellent structure | Reasonable definition | Excellent structure |
| Example 3 | Dark blue in cell wall (Cell death) | Dark blue in cell wall and light blue cytoplasm (Cell death) | Excellent structure | Excellent structure | Excellent structure | Reasonable definition | Good structure |
| Example 4 | Dark blue in cell wall (Cell death) | Dark blue in cell wall and light blue cytoplasm (Cell death) | Excellent structure | Excellent structure | Excellent structure | Poor definition | Excellent structure |
| Example 5 | Dark blue in cell wall (Cell death) | Dark blue in cell wall and dark blue cytoplasm (Cell death) | Excellent structure | Excellent structure | Excellent structure | Reasonable definition | Excellent structure |
| Example 6 | Dark blue in cell wall (Cell death) | Dark blue in cell wall and light blue cytoplasm (Cell death) | Excellent structure | Excellent structure | Excellent structure | Reasonable definition | Excellent structure |
| Example 7 | Dark blue in cell wall (Cell death) | Dark blue in cell wall and light blue cytoplasm (Cell death) | Excellent structure | Excellent structure | Excellent structure | Good definition | Good structure |

TABLE 1.0-continued

| Fixative | Cell viability after 2 mins (Trypan blue) | Cell viability after 24 hours (Trypan blue) | Cell structure after 24 hours (Lugol's Iodine) | Cell structure after 48 hours (Lugol's Iodine) | Cell structure after 1 week (Lugol's Iodine) | Cell structure after 1 week (Trichrome stain) | Cell structure after 2 months (Lugol's Iodine) |
|---|---|---|---|---|---|---|---|
| Example 8 | Dark blue in cell wall (Cell death) | Dark blue in cell wall and light blue cytoplasm (Cell death) | Excellent structure | Excellent structure | Excellent structure | Excellent definition | Excellent structure |
| Example 9 | Dark blue in cell wall (Cell death) | Dark blue in cell wall and light blue cytoplasm (Cell death) | Excellent structure | Excellent structure | Excellent structure | Good definition | Good structure |
| Example 10 | Dark blue in cell wall (Cell death) | Dark blue in cell wall and light blue cytoplasm (Cell death) | Excellent structure | Excellent structure | Excellent structure | Good definition | Good structure |
| Example 11 | Dark blue in cell wall (Cell death) | Dark blue in cell wall and dark blue cytoplasm similar to Alcorfix (Cell death) | Excellent structure | Acceptable structure | Excellent structure | Poor definition | |

The fixatives of Examples 5 to 11 gave particularly good results, with the Example 8 formulation currently being considered the best.

Preferred aqueous fixative solutions of the present invention can be used with e.g. faecal parasite concentrator devices.

Such devices are commercially available e.g. as the Parasep® or ParaPRO® devices or the devices shown in WO2017/187165A, in the name of the present applicants, for example.

Such devices typically utilise a mixing chamber and a receiving chamber separated by a filter.

In use, a fixative solution and a faecal sample are introduced into the mixing chamber and agitated in contact to liquefy the sample. The liquified sample is then filtered and the filtrate, (containing e.g. ova and cysts which pass through the filter) is collected in the receiving chamber.

The fixative solution ensures that the filtrate is not biologically hazardous. The filtrate can then be examined under the microscope to identify e.g. the ova and cysts.

For example, a mini Parasep® device can be used, which will typically hold 3.3 ml of fixative solution within the mixing tube. A 0.5-1.0 g sample of stool is added to the mixing tube before the tube is sealed with a vertical filter attached to a sedimentation tube. The sample is then vortexed, inverted and typically centrifuged for 2 minutes at 400 g (dependent on filter version). The filter and mixing tube can then be removed and a sample taken from the pellet found at the base of the sedimentation tube. This is then mounted on a microscope slide, where a stain may be added before the sample is examined for the presence of parasitic organisms.

In some cases, it is desirable for the fixative solution to float the ova and cysts so that they can be more readily identified and separated from the solution. Such solutions are known as flotation solutions.

Such flotation solutions can for example be used in a mini Parasep® device as follows:

A 0.5-1.0 g sample of stool is added to the mixing tube before the tube is sealed with a vertical filter attached to a sedimentation tube. The sample is then vortexed, inverted and squeezed by hand to pressurise the vessel, forcing the filtration of the sample. The solution is left to rest for 3 minutes, before an inoculation loop is used to remove a layer from the top of the liquid (which will be holding the majority of the parasitic ova and cysts if present). This is then mounted on a microscope slide, where a stain may be added before the sample is examined for the presence of parasitic organisms.

The following Examples relate to formulations of flotation solutions. The volumes of fixative are approximate whereas the masses and (in the case of glacial acetic acid) volume of the components are exact. The specific gravity values (density compared to pure water) are also exact.

A series of high specific gravity fixative solutions were prepared as follows:

Example 13

Approximately 500 ml of fixative was prepared with the following formulation:
231.25 ml de-ionised water
250 g cane sugar
18.75 ml of Glacial Acetic Acid (3.75 v/v % solution—0.66M)

0.45 g Sodium Benzoate—0.09% (6.25 mM)
2.25 g Calcium Chloride—0.45% (0.041M)
2.25 g Calcium Bromide hydrate—0.41% (0.021M)
0.025 g Menthol—0.005%
0.0875 g Thymol—0.0175%
The specific gravity of the resulting fixative was 1.265.

This formulation was one of the most effective of the high density formulations in Examples 13 to 28. In a variant of this formulation (Example 28), a higher proportion of cane sugar was employed in order to raise the specific gravity of the fixative solution to about 1.29.

Example 14

Approximately 500 ml of fixative was prepared with the following formulation:
231.25 ml de-ionised water
250 g cane sugar
18.75 ml of Glacial Acetic Acid (3.75 v/v % solution—0.66M)
1.8 g Sodium Benzoate—0.36% (25 mM)
40 g Calcium Chloride—8.0% (0.72M)
2.25 g Calcium Bromide hydrate—0.41% (0.021M)
0.025 g Menthol—0.005%
0.0875 g Thymol—0.0175%
The specific gravity of the resulting fixative was 1.245.

Example 15

Approximately 500 ml of fixative was prepared with the following formulation:
231.25 ml de-ionised water
230 g cane sugar
18.75 ml of Glacial Acetic Acid (3.75 v/v % solution—0.66M)
0.5 g Sodium Benzoate—0.10% (6.9 mM)
60 g Calcium Chloride—12.0% (1.08M)
2.25 g Calcium Bromide hydrate—0.41% (0.021M)
0.025 g Menthol—0.005%
0.0875 g Thymol—0.0175%
The specific gravity of the resulting fixative was 1.272

Example 16

Approximately 500 ml of fixative was prepared with the following formulation:
231.25 ml de-ionised water
200 g cane sugar
18.75 ml of Glacial Acetic Acid (3.75 v/v % solution—0.66M)
0.5 g Sodium Benzoate—0.10% (6.9 mM)
60 g Calcium Chloride—12.0% (1.08M)
2.25 g Calcium Bromide hydrate—0.41% (0.021M)
0.025 g Menthol—0.005%
0.0875 g Thymol—0.0175%
The specific gravity of the resulting fixative was 1.297.

Example 17

Approximately 500 ml of fixative was prepared with the following formulation:
231.25 ml de-ionised water
180 g cane sugar
18.75 ml of Glacial Acetic Acid (3.75 v/v % solution—0.66M)
0.25 g Sodium Benzoate—0.050% (3.5 mM)
80 g Calcium Chloride—16.0% (1.44M)

2.25 g Calcium Bromide hydrate—0.41% (0.021M)
0.025 g Menthol—0.005%
0.0875 g Thymol—0.0175%
The specific gravity of the resulting fixative was 1.324.

Example 18

Approximately 850 ml of fixative was prepared with the following formulation:
462.5 ml de-ionised water
200 g cane sugar
37.5 ml of Glacial Acetic Acid (4.4 v/v % solution—0.66M)
0.50 g Sodium Benzoate—0.059% (3.5 mM)
390 g Calcium Chloride dihydrate—34.7% (3.12M)
4.5 g Calcium Bromide hydrate—0.48% (0.024M)
0.050 g Menthol—0.0059%
0.175 g Thymol—0.021%
The specific gravity of the resulting fixative was 1.310.

Example 19

Approximately 400 ml of fixative was prepared with the following formulation:
231.25 ml de-ionised water
50 g cane sugar
18.75 ml of Glacial Acetic Acid (4.7 v/v % solution—0.82M)
0.25 g Sodium Benzoate—0.063% (4.33 mM)
250 g Calcium Chloride dihydrate—47.1% (4.25M)
2.25 g Calcium Bromide hydrate—0.52% (0.026M)
0.025 g Menthol—0.0063%
0.0875 g Thymol—0.022%
The specific gravity of the resulting fixative was 1.360.

Example 20

Approximately 450 ml of fixative was prepared with the following formulation:
231.25 ml de-ionised water
25 g cane sugar
21 ml of Glacial Acetic Acid (4.7 v/v % solution—0.82M)
0.25 g Sodium Benzoate—0.055% (3.89 mM)
250 g Calcium Chloride dihydrate—42.0% (3.78M)
2.25 g Calcium Bromide hydrate—0.46% (0.023M)
0.025 g Menthol—0.0056%
0.0875 g Thymol—0.019%
The specific gravity of the resulting fixative was 1.330.

Example 21

Approximately 850 ml of fixative was prepared with the following formulation:
462.5 ml de-ionised water
360 g cane sugar
37.5 ml of Glacial Acetic Acid (4.4 v/v % solution—0.77M)
0.50 g Sodium Benzoate—0.059% (4.08 mM)
200 g Calcium Chloride dihydrate—17.8% (1.60M)
4.5 g Calcium Bromide hydrate—0.49% (0.024M)
0.050 g Menthol—0.0059%
0.175 g Thymol—0.021%
The specific gravity of the resulting fixative was 1.308.

Example 22

Approximately 950 ml of fixative was prepared with the following formulation:

550 ml de-ionised water 360 g cane sugar 37.5 ml of Glacial Acetic Acid (3.9 v/v % solution—0.69M)

200 g Calcium Chloride dihydrate—15.9% (1.43M)

4.5 g Calcium Bromide hydrate—0.44% (0.022M)

0.050 g Menthol—0.0053%

0.175 g Thymol—0.018%

The specific gravity of the resulting fixative was 1.280.

Example 23

Approximately 820 ml of fixative was prepared with the following formulation:

500 ml de-ionised water 280 g cane sugar 37.5 ml of Glacial Acetic Acid (4.5 v/v % solution—0.80M)

200 g Calcium Chloride dihydrate—18.4% (1.66M)

4.5 g Calcium Bromide hydrate—0.51% (0.025M)

0.050 g Menthol—0.0061%

0.175 g Thymol—0.021%

The specific gravity of the resulting fixative was 1.270.

Example 24

Approximately 800 ml of fixative was prepared with the following formulation:

500 ml de-ionised water 200 g cane sugar 37.5 ml of Glacial Acetic Acid (4.9 v/v % solution—0.82M)

240 g Calcium Chloride—30.9% (2.70M)

4.5 g Calcium Bromide hydrate—0.52% (0.027M)

0.050 g Menthol—0.0063%

0.175 g Thymol—0.022%

The specific gravity of the resulting fixative was 1.330.

Example 25

Approximately 420 ml of fixative was prepared with the following formulation:

231.25 ml de-ionised water 100 g cane sugar 18.75 ml of Glacial Acetic Acid (4.5 v/v % solution—0.78M)

0.45 g Sodium Benzoate—0.11% (7.44 mM)

15 g Calcium Chloride—3.57% (0.32M)

2.25 g Calcium Bromide hydrate—0.49% (0.025M)

0.025 g Menthol—0.0059%

0.0875 g Thymol—0.021%

30 g Citric acid—7.1% (0.037M)

The specific gravity of the resulting fixative was 1.288.

Example 26

Approximately 400 ml of fixative was prepared with the following formulation:

250 ml de-ionised water 100 g cane sugar 20.0 ml of Glacial Acetic Acid (5.0 v/v % solution—0.87M)

0.45 g Sodium Benzoate—0.11% (7.44 mM)

90 g Calcium Chloride—22.5% (2.03M)

2.25 g Calcium Bromide hydrate—0.52% (0.026M)

0.025 g Menthol—0.0063%

0.0875 g Thymol—0.022%

60 g Citric acid—15.0% (0.78M)

The specific gravity of the resulting fixative was 1.296.

Example 27

Approximately 420 ml of fixative was prepared with the following formulation:

250 ml de-ionised water 50 g cane sugar 20.0 ml of Glacial Acetic Acid (4.8 v/v % solution—0.83M)

0.45 g Sodium Benzoate—0.11% (7.44 mM)

200 g Calcium Chloride dihydrate 36.0% (3.24M)

2.25 g Calcium Bromide hydrate 0.49% (0.025M)

0.025 g Menthol—0.0059%

0.0875 g Thymol—0.021%

60 g Citric acid—14.3% (0.74M)

The specific gravity of the resulting fixative was 1.337.

Example 28

Approximately 5100 ml of fixative was prepared with the following formulation:

2300 ml de-ionised water 3750 g cane sugar 375 ml of Glacial Acetic Acid (7.4 v/v % solution—1.3M)

4.5 g Sodium Benzoate—0.88% (6.1 mM)

60 g Calcium Chloride—1.2% (0.11M)

30 g Calcium Bromide hydrate 0.59% (0.027M)

0.25 g Menthol—0.049%

0.875 g Thymol—0.017%

The specific gravity of the resulting fixative was approximately 1.29.

This SG formulation is the most preferred of Examples 14 to 28.

Magnesium halides may be substituted for the calcium halides in the Examples.

It is considered that similar results would be obtained if the concentrations of the acetic acid in the Examples were varied by about ±0.3M or more and that acceptable results would be obtained over broader ranges as defined in the claims. It is considered that similar results would be obtained if the concentrations of the remaining components in the Examples were varied by at least ±10%, possibly ±20% or more of their stated values and that acceptable results would be obtained over a wider range of concentrations.

In general, the upper limit of halide salt concentration is set only by the solubility of each particular salt in the fixative solution.

The invention claimed is:

1. An aqueous fixative solution for biological samples comprising:

a) a $C_2$ to $C_6$ carboxylic acid at a concentration of 0.9M or greater;

b) an alkaline earth halide salt at a concentration of 0.02M or greater; and c) a biocidal essential oil component in a concentration of at least 50 µg/ml, wherein the aqueous fixative solution is alcohol free.

2. An aqueous fixative solution for biological samples consisting of:

a) a $C_2$ to $C_6$ carboxylic acid at a concentration of 0.9M or greater;

b) an alkaline earth halide salt at a concentration of 0.02M or greater;

c) a biocidal essential oil component in a concentration of at least 50 µg/ml; and optionally one or more of:

d) a bacteriostatic or fungistatic concentration of benzoic acid or sorbic acid or a salt thereof;

e) a soluble carbohydrate;

f) citric acid; and g) a surfactant.

3. An aqueous fixative solution for biological samples comprising:

a) a $C_2$ to $C_6$ carboxylic acid at a concentration of 0.9M or greater;

b) an alkaline earth halide salt at a concentration of 0.02M or greater;

c) a biocidal essential oil component in a concentration of at least 50 µg/ml; and d) a bacteriostatic or fungistatic concentration of benzoic acid or sorbic acid or a salt thereof, wherein:

i) said carboxylic acid component a) is acetic acid at a concentration of 0.9M to 1.75M;

ii) said alkaline earth halide salt component b) is calcium chloride at a concentration of 70 mM to 100 mM plus calcium bromide at a concentration of 30 mM to 50 mM; and iii said component (d) is a benzoic acid salt at a concentration of 5 mM to 15 mM benzoate.

4. An aqueous fixative solution for biological samples comprising:

a) a $C_2$ to $C_6$ carboxylic acid at a concentration of 0.9M or greater;

b) an alkaline earth halide salt at a concentration of 0.02M or greater;

c) a biocidal essential oil component in a concentration of at least 50 µg/ml; and d) a bacteriostatic or fungistatic concentration of benzoic acid or sorbic acid or a salt thereof, wherein:

i) said carboxylic acid component a) is acetic acid at a concentration of 1.2M to 1.75M;

ii) said alkaline earth halide salt component b) is calcium chloride at a concentration of 70 mM to 100 mM plus calcium bromide at a concentration of 30 mM to 50 mM; and iii) said component (d) is a benzoic acid salt at a concentration of 5 mM to 15 mM benzoate.

5. An aqueous fixative solution for biological samples comprising:

a) a $C_2$ to $C_6$ carboxylic acid at a concentration of 0.9M or greater;

b) an alkaline earth halide salt at a concentration of 0.02M or greater;

c) a biocidal essential oil component in a concentration of at least 50 µg/ml; and d) a bacteriostatic or fungistatic concentration of benzoic acid or sorbic acid or a salt thereof, wherein:

i) said carboxylic acid component a) is acetic acid at a concentration of 0.9M to 1.75M;

ii) said alkaline earth halide salt component b) is calcium chloride and/or calcium bromide at a total concentration of from 1.0M to 4.5M; and iii) said component (d) is a benzoic acid salt at a concentration of 5 mM to 125 mM benzoate.

\* \* \* \* \*